United States Patent
Ward (10) Patent No.: US 8,915,132 B1
(45) Date of Patent: Dec. 23, 2014

(54) VISUAL WARNING DEVICE FOR WEIGHT BEARING

(71) Applicant: Frederick Albert Ward, Cairo, MO (US)

(72) Inventor: Frederick Albert Ward, Cairo, MO (US)

(73) Assignee: Physical Therapy Services, LLC, Cairo, MO (US)

(*) Notice: Subject to any disclaimer, the term of this patent is extended or adjusted under 35 U.S.C. 154(b) by 0 days.

(21) Appl. No.: 13/694,423

(22) Filed: Nov. 30, 2012

(51) Int. Cl.
*A61B 5/00* (2006.01)
*G01L 7/00* (2006.01)
*A61B 5/103* (2006.01)

(52) U.S. Cl.
CPC ............................ *A61B 5/103* (2013.01)
USPC ............................................ 73/172; 73/700

(58) Field of Classification Search
None
See application file for complete search history.

(56) References Cited

U.S. PATENT DOCUMENTS

| | | | |
|---|---|---|---|
| 2,558,805 A | 7/1951 | Yaglou | |
| 3,702,999 A | 11/1972 | Gradisar | |
| 3,791,375 A | 2/1974 | Pfeiffer | |
| 3,974,491 A | 8/1976 | Sipe | |
| 4,557,257 A * | 12/1985 | Fernandez et al. | 602/5 |
| 4,647,918 A | 3/1987 | Goforth | |
| 4,745,930 A | 5/1988 | Confer | |
| 4,858,620 A | 8/1989 | Sugarman et al. | |
| 5,107,854 A | 4/1992 | Knotts et al. | |
| 5,253,654 A | 10/1993 | Thomas et al. | |
| 5,269,081 A | 12/1993 | Gray | |
| 5,285,022 A | 2/1994 | Antone | |
| 5,357,696 A | 10/1994 | Gray | |
| 5,619,186 A | 4/1997 | Schmidt et al. | |
| 5,642,096 A | 6/1997 | Leyerer et al. | |
| 5,775,332 A | 7/1998 | Goldman | |
| 6,030,351 A | 2/2000 | Schmidt et al. | |
| 6,087,926 A | 7/2000 | Hajianpour | |
| 6,174,294 B1 | 1/2001 | Crabb et al. | |
| 6,405,606 B1 | 6/2002 | Walczyk et al. | |
| 7,878,990 B2 | 2/2011 | Al-Obaidi et al. | |
| 7,998,092 B2 | 8/2011 | Auni et al. | |
| 2006/0206167 A1* | 9/2006 | Flaherty et al. | 607/48 |
| 2008/0029139 A1* | 2/2008 | Pijanowski | 135/67 |
| 2008/0167580 A1 | 7/2008 | Auni et al. | |
| 2011/0130686 A1 | 6/2011 | Fenkell | |
| 2011/0214501 A1 | 9/2011 | Ross | |

* cited by examiner

*Primary Examiner* — Andre Allen
(74) *Attorney, Agent, or Firm* — Armstrong Teasdale LP (57) ABSTRACT

An improved weigh bearing monitor determining weight or urge applied upon an impaired lower extremity when limited weight bearing is prescribed by a medical professional. The limited amount of weight borne on the affected limb visualized on gauge (3) attached to assistive walking device (4) with weight borne readable on gauge (3) located within visual range of the user or caregiver. The device consists of gauge (3) connected to assistive walking device (4) connected by hose or tube (2) to foot appendage component containing bladder (1) attached to user's (6) foot. When user (5) applies pressure upon bladder (1), then gauge (3) is in view of user (5) or caregiver monitoring weight applied to the affected limb. This device may also be wireless with elimination of the hose. This device may also be hydraulic or pneumatic in accordance with variation maintaining the visual ability of user or caregiver.

17 Claims, 3 Drawing Sheets

VISUAL WARNING DEVICE FOR WEIGHT BEARING

CROSS REFERENCE TO RELATED APPLICATIONS

Not Applicable

FEDERALLY SPONSORED RESEARCH

Not Applicable

1. Field

This application relates to a device providing the ability to visually monitor the amount of weight being placed on a user's foot when a medical professional prescribes weight bearing limits.

2. Present Methods for Control of Weight Bearing

The human being is bipedal. When establishing a gait pattern, weight is shifted with the entire weight of the body applied to one extremity, called the stance phase of walking, while the other extremity moves through a swing phase. When the swing phase is concluded, the swinging lower extremity begins weight bearing, generally referred to as the stance phase, while the opposing lower extremity moves through a swing phase.

Often, after injury, orthopedic surgery, ulceration or other lesion of the foot, a physician may require the patient to limit the amount of weight placed on one foot, with the limitation for a specified period of time, to reduce risk of further injury or damage to the affected body part. As the patient progresses toward "full" weight bearing on the affected leg, the physician may prescribe increases in the amount of weight applies to the incapacitated extremity.

As an example, the physician may call for weight bearing of 25 percent of body weight or a designated amount of weight, such as 30 or 40 pounds. Crutches or a walker may be employed to assist in weight limiting by supporting body weight with upper extremity and upper body strength. Generally, it is the responsibility of a health professional, for example, a licensed physical therapist, to determine if the prescribed amount of weight is being controlled.

Presently, there are four methods of monitoring weight bearing on a patient who has been prescribed limited weight bearing on one extremity. The four methods utilized are:

1. Ask the patient to place the affected foot on a bathroom scale and apply pressure until the required restriction is met. For example, 20 pounds of weight. The patient applies sufficient urge until 20 pounds is registered on the scale. Then repeat the practice session until the user is confident they understand the amount of pressure borne on that foot. The high probability of risk is that it is difficult, near impossible to remember that specific sensation of urge prescribed the next time you ambulate.

2. The assisting caregiver places his/her foot under the patient's affected foot and monitor pressure caused as the patient steps. The complications with this method is the therapist or caregiver monitoring weight bearing is in danger of injuring his/her foot. There is awkwardness or inaccurate estimation of urge prescribed, and inability of the user to continue ambulating without the support of the caregiver.

3. Use a monitor attached to the foot being monitored. The monitor presently utilized and noted in prior art will produce a sound or vibration when the desired load is exceeded. There is risk of further injury when excessive urge has been applied after the sound or vibration engages. Also, as in the occurrence of dementia, the user or assisting caregiver may not hear or feel the warning. There is further risk of exceeding weight limits if the power source required for emitting sound or vibration fails without the user realizing it is not responding. A majority of therapy providers rarely use this device because it may be prohibitively expensive or used by more than one patient, creating risk of cross contamination or infection. This will be discussed when reviewing prior art.

4. Require the patient to walk without pressure on the affected extremity or "hop" while using a walker or crutches. Problems associated with inability to hop are age and co-morbidities. Examples are arthritis in the hands and shoulders, balance deficits and debility.

3. Discussion of Prior Art

U.S. Pat. No. 2,558,805 to Yaglou (1951) Yaglou teaches a device with the "specific object of the present invention to provide apparatus for the measurement of pressure inside a shoe or other garment on the body of the wearer." The patent description of the device and Claims presented, Yaglou utilized bladders and an electrical system to accomplish the goal of monitoring the pressures inside a garment or shoe in order to determine fit and sizing with an emphasis on shoes. There is no indication Yaglou, skilled in the art, ever intended this device be used for observing urge applied through weight bearing of a lower limb because it was unobvious to the inventor.

U.S. Pat. No. 3,702,999 to Gradisar (1972) teaches "A device for warning a patient when he exceeds a predetermined amount of weight on his foot during locomotion comprising two force-sensitive electrical contactors disposed one each in predetermined positions beneath the heel and ball of the foot. The contactors are secured in a thin pad shaped to conform to the bottom of the shoe or footwear of the patient. Each electrical contactor includes a pair of flat circular metal plates separated by a resilient member and connected to a battery-powered alarm." In reviewing the patent it is noted in Drawing—FIG. 1, the signal box is located near or above the shoe. Claims from Number 1 through Number 21, Gradisar did not specifically identify the placement or position of the signaling device in relationship to the shoe portion of the device. Utilizing electrical current for actuating an alarm indicates a battery is employed in the invention and the alarm is audible raising the question of power failure and hearing deficits of the user and/or caregiver. If the source of energy fails, there is no indication of excessive urge being applied and the risk of further injury is eminent. At no time did Gradisar, although skilled in the art, anticipate using the device claimed for visually monitoring weight bearing with a gauge or Liquid-crystal Diode (herein referred to as LCD) located on an assistive walking device because it was unobvious to the inventor.

U.S. Pat. No. 3,791,375 to Pfeiffer (1974) teaches a "device comprises a load cell which has upper and lower substantially inflexible plates joined around their periphery by resilient means which deflects in accordance with the load applied to the plates. Deflection detecting means indicates when a predetermined load is obtained. In the preferred embodiment, the plates are sealed with respect to each other around their periphery, and the volume there between is connected to a displacement-measuring device. The displacement-measuring device is preferably a remote bellows which actuates an alarm upon predetermined displacement." Pfeiffer discloses "a fluid-containing load cell which deflects and changes in volume, in accordance with the amount of load thereon. A tubular connector connects the load cell fluid with a displacement-measuring device, for example, a bellows. A particular displacement limit, conveniently signaled with an electrical alarm indicates when predetermined load on the cell is reached." Pfeiffer claims "there being no signal below the determined ambulation force load and a warning signal above the predetermined ambulation force load." This "audible signal" will sound only when the desired limitation of urge has been reached or exceeded causing exposure of further insult to the affliction. The alarm being electrical requires a source of energy not readily identifiable in drawings or description is assumed to be a battery. In the event of energy failure, the device would fail to alarm without the user recognizing the malfunction. Failure of the alarm would cause risk of excessive urge on the extremity causing potential injury. It is possible this device may leak from the fluid cell causing a slipping hazard and risk of injury. The device demonstrated in FIG. 1 is attached to the user at the ankle and relies on the user or caregiver hearing the alarm. This is a critical issue. In the Claims, the inventor fails to indicate the appropriate placement or possible other placements of the "audible signal device". A high percentage of users and/or caregivers (often spouses) will be hard of hearing as a co-morbidity. At no time did Pfeiffer, skilled in the art, anticipate the use of a gauge or LCD or the placement of the gauge or LCD within view of the user or caregiver because it was unobvious to this inventor.

U.S. Pat. No. 3,974,491 to Sipe (1976) teaches "a resilient foot pad having a toe end and a heel end and adapted to substantially cover the inner sole of a shoe." The inventor further discloses "A resilient liquid filled tube mounted within the pad" and further explains "A signaling device is controlled by a pressure responsive means in communication with the liquid in the tube for the actuation of the signaling means at a predetermined pressure of said liquid. As described in Pfeiffer, above, there is no indication when weight bearing has been exceeded to a point of risk. The device relies on a battery for source of energy and is fluid filled. Further examination of this patent shows in drawing, FIG. 1, it as attached to the user at the lower leg or ankle level. This device teaches an "adjustable means" to alter the amount of urge causing the signal to actuate. Failure in the adjusting component may cause the wrong designated urge to be monitored. Reviewing the concerns one must recognize the possibility of fluid leaking, failure of the energy source and the user having a hearing deficit as well as failure to adjust the level of urge monitored. Mr. Sipe's claims, skilled in the art, did not anticipate using a gauge or LCD attached to an assistive walking device for visual monitoring because it was unobvious to this inventor.

U.S. Pat. No. 4,648,918 to Goforth (1987) teaches monitoring over a period of time weight bearing by multi-event notification regarding conditions such as diabetes and, after review, is not considered because it does not allow for monitoring during ambultion.

U.S. Pat. No. 4,745,930 to Confer (1988) claims disclose "A flexible force sensing insole adapted to be placed inside a shoe to permit an analysis of the walking or running gait of the wearer," etc. In the BACKGROUND OF THE INVENTION, Confer further discloses "A device of this general type is currently marketed by Chattex Corporation of Chattanooga, Tenn., under the trademark "TRIAX". Further stated in the BRIEF DESCRIPTION OF THE DRAWINGS, column 3, line 10, "The signals from the three potentiometers are fed through wires to a transmitter that is attached to a central computer (not shown), which collects and analyzes the data and prints a report on a strip sheet." In conclusion, Confer is teaching a device for analysis of a gait pattern involving a force sensing device of a walker or a runner, not a person recovering from an injury specifically. Although skilled in the art, it was unobvious and not in the inventor's interest to attach an LCD or gauge to an assistive walking device to visually monitor weight bearing when limited weight bearing has been prescribed.

U.S. Pat. No. 4,858,620 to Sugerman et al. (1989) teaches "A small, inexpensive, but reliable pressure warning system includes a plurality of pressure sensors which are disposed between an orthopedic restraining member and an injured portion of a patient's body, and a processor and alarm unit coupled to the pressure sensor and providing a warning when the pressure reaches a danger level (i.e. 30 mm)" and teaches "The processor and alarm unit can be mounted directly on the patient's cast and are disposable, one-use items." Sugerman et al. claims, "An apparatus for monitoring pressure beneath an orthopedic restraining device that has been applied to a person's body" (said cast). The apparatus having means to indicate a warning that may include a numerical indication if said output signal or an audible alarm set at a predetermined level or an indicator with a series of lights indicating differing values of orthopedic pressures. Electrical means requiring a battery for a source of energy. It was unobvious to the inventors et al., while skilled in the art, to utilize an LCD or gauge attached to an assistive walking device to be observed by a user or caregiver as the device described was intended to be "mounted directly on the patient's cast".

U.S. Pat. No. 5,107,854 to Knotts et al (1992) teaches "An orthopedic exercise chamber such as a slipper including a light-weight, self-contained limb load monitor is disclosed. The limb load sensor circuit provides extended service life for the miniature power supply that is included in the slipper, thereby making the slipper suitable for out-patient use. A fluid-filled plantar chamber that supports the entire load borne by the patient's foot is connected to the sensor circuit, thereby providing improved monitoring of the load being carried by the leg or foot that must be protected from excessive loading." The drawing identified as FIG. 3 shows the placement of the electronics assembly 107 attached to the user's shoe assembly and is assumed attachable to the ankle or lower leg driven by "two 3-volt coin size batteries" (column 4, line 59) and is also described as "provide reliable monitoring for a period of 90 to 120 days of continuous use before requiring battery replacement." (column 4, line 62). In brief, the device describes a pressure-sensing device comprising a fluid filled chamber, an electronic assembly comprising a sensor, a comparator circuit and an alarm circuit with an electrical source which emits sound or vibration when the desired load or weight has been exceeded. The user may or may not feel the vibration or hear the sound causing the weight being monitored to be exceeded. Due to the complication of the circuitry, any component may fail without the user recognizing the hazard of excessive urge. Again we can suspect fluid leakage, source of energy failure, loss of hearing and co-morbidities causing loss of sensation in the lower extremity, such as Diabetes Mellitus. In regard to Knotts et al. claims; What is claimed in Claim number 11, (column 8, line 14) "means for indicating when said predetermined pressure limit has been exceeded." No indication of what form of "means for indicating" is described and is assumed to be a sound, buzzer or bell or vibration. Although skilled in the art, the concept of placing an LCD or gauge on an assistive walking device for visual monitoring was unobvious to Knotts et al. U.S. Pat. No. 5,253,654 to Thomas et al (1993) teaches "An orthopedic weight monitor for detecting weight bearing forces on a lower extremity for orthopedic purposes", etc. The inventor describes a device in brief "comprising in combination: flexible pad means shaped for conforming to the bottom of a foot for placement inside of a shoe, the pad means having a heel portion positionable beneath the heel of a user: sensor means encased within the heel portion of the pad means to be located beneath the heel of the user, the sensor means comprising a thin, rigid rectangular plate means, the plate having opposed edges which minimize deflection of the plate means about an axis extending from one opposed edge to the other and a foil strain gauge means coupled therebeneath; electronic module means remotely positioned from the sensor means to receive signals from the foil strain gauge means; and communication means between the sensor means and the electronic module means." The inventor et al further describes the communication to be emitting a signal, preferably a sound, or the signal may consist of a vibration or other continuous analog or digital display. However, the display is not deliberately placed in a position where the user or observer can see his or her own amount of weight bearing. This is shown in FIG. 1 and FIG. 6 to be attached at the waist of the user. In spite of the fact that the inventor was skilled in the art, it was unobvious to Thomas et al. to monitor the force described with an LCD or gauge attached to an assistive walking device.

U.S. Pat. No. 5,269,081 to Gray (1993) teaches "A force monitoring shoe for monitoring the force being applied to a patient's leg, as during walking." And teaches "When force equal to a selectable value has been applied, an alert system notifies the patient." As Shown in FIG. 1, Number 20, and described in Column 3, line 38 as part of the preferred embodiment, the alert system is described as "a vibrational means 20 is employed as the signaling device" and is located on the 10 monitoring shoe. In Gray's claims, the alert system is described as a "vibrational motor with an under surface of said covering member to produce vibrations against a bottom of the wearer's foot" (Column 9, line 35). This device requires a battery for a source of energy. It does not claim sound as a signal and by utilizing vibration as the alarming force discounts as users, patient's with a loss of sensation in their lower extremities as seen in advanced Diabetes Mellitus. Gray also discusses the use of a walker, however, he does not identify the use of any signalling attachment to the walker in his Claims. Although, skilled in the art, inventor Gray was unobvious of the concept of employing an LCD or gauge to visually monitor force applied to an assistive walking device.

U.S. Pat. No. 5,285,022 to Antone (1994) teaches "A partial weight-bearing scale including a planer weighing surface and a fixed load supporting platform to one side of the weighing surface." This is not considered because it is not attached to the lower limb and is not capable of being mobilized with the user. Antone had no intention of having his device mounted on an assistive walking device.

U.S. Pat. No. 5,357,696 to Gray et al. (1994) teaches, "The device includes a pressure sensitive element that produces an electrical signal that is related to the force, with this signal being used to alert the wearer when a force in excess of a preselected value occurs." In the section titled "BEST MODE FOR CARRYING OUT THE INVENTION", Gray et al comments but does not add to the drawings "Typically, those components used to alert a user will be mounted within an enclosure than can be attached to, or be a part of, a patient-assist structure (walker, etc.), not shown. The inventor further teaches "There can be sound devices (buzzers or beepers), electrical impulses, or some form of light display (LED array). The inventor, skilled in the art, does not specifically note the concept of attaching a gauge or LCD to the walker, indicating urge borne, in a position for visualization by the user or a caregiver nor does the inventor imply the use of a bladder without electrical energy as my device describes.

U.S. Pat. No. 5,619,186 to Schmidt et al. also teaches a "device comprising a power supply, at least one resistive force sensor, signal conditioning means, calibrating means, programming means and alarm generating means." In a review of Schmidt et al. claims, it is noted that accommodation for an alarm "wherein said alarm varies in volume, frequency and intermittency" is so stated several times. And in claims, the statement "further comprising a data cable whereby said data is used to connect said calibrating means to said programming means." There is no reference to the location or origin of the alarm noted as veriable in "volume, frequency and intermittency". At no point in the claims does it mention the location of the sound device because, although skilled in the art, it was unobvious to Schmidt et al. that an LCD or gauge could be attached to an assistive walking device for visual monitoring by the user or a caregiver.

U.S. Pat. No. 5,642,096 to Leyerer, et al. (1997) teaches "A device for prevention of ulcers in the feet of diabetes patients is embodied in a footwear article such as a shoe. The device includes a sensor disposed in a contained liquid mass of a hydrocell carried in the shoe inner sole, the sensor being one that detects both pressure and temperature values to which the patient's feet are exposed." The device utilizes piezoresistors with an electrical bridge as "means for detecting a pressure change in said hydrocell". This message described as "wherein a readily discernible, audible or visual signaller 28 is located, can be carried by the patient, hooked on a belt, hung by a strip about the neck or other means as facilitates the patient having the processor in manner as to be made aware of warning signalling." The inventors, skilled in the art, did not anticipate attaching the device to an assistive walking device, observable by the user or a caregiver, although patients with diabetes may also be afflicted with forgetfulness, loss of hearing or dementia and require constant monitoring because it was unobvious that this user may also need an assistive walking device.

U.S. Pat. No. 5,775,332 to Goldman (1998) teaches "A capacitive biofeedback sensor including a polyurethane dielectric sandwiched between two wire mesh or carbon impregnated silicone rubber conductors". Further described "The sensor is placed within a patient's shoe, boot, ankle, brace, crutch, hand grip, wheelchair, etc., and provides biofeedback to help patients relearn function or prevent complications that impede function."

Goldman also teaches "biofeedback may provide for monitoring the weight applied to a limb ("limb load monitoring")" and adds "relates to limiting the weight that is borne by the limb when recovering from leg fracture or joint replacement." In claim 2, the inventor claims "(a) a buzzer, wherein said buzzer emits auditory tones according to the relation between said capacitance and said preset value, thereby imparting auditory feedback to a user." The inventor, skilled in the art, did not consider deafness or forgetfulness and the potential need for a caregiver to visually observe the level of monitoring required by the patient because it was unobvious that an LCD or gauge attached to an assistive walking device could be employed.

U.S. Pat. No. 6,030,351 to Schmidt et al (2000) teaches "A pressure relief reminder and compliance system and method to prevent the formation of pressure sores on a person's skin is disclosed." This device includes "a sensor which responds according to pressure exerted on the skin; a programmable microcontroller connected to the sensor" which is then downloaded to memory for review and analysis by a physician. The inventors, skilled in the art, did not consider having a visible method such as a gauge or LCD for the user or a caregiver to view. This is the significant objective of my device.

U.S. Pat. No. 6,087,924 to Hajianpour (2000) discloses in the Abstract "Apparatus is configured to provide an alarm perceivable by a user when an increase in a level of force applied to a foot exceeds a threshold value determined by a variable resistance." The inventor further explains, "This pressure is converted into an electrical signal within a pressure transducer in an insole within a control box, and "the result of this comparison is used to determine when the alarm is provided." Further examination of the patent, referring to FIG. 4, "the control box 28 additionally includes an external hook 44 facilitating carrying the control box 28 attached to a belt." There is noted that when the battery is low on electrical current, a constant alarm is given through the beeper 69 to warn that the battery should be replaced. Further more, it is noted the beeper may be replaced with a device "producing predominantly vibrations instead of audible signal."

Again, the inventor, skilled in the art, has not considered deafness of the user or caregiver and does not specify when the vibratory element will be employed. There is no comparison with the device I have because at no time did the inventor consider an alternative of a gauge or LCD for visually observing the amount of weight the user is applying to the limb.

U.S. Pat. No. 6,405,606 to Walczyk (2002) teaches "A mechanical weight bearing indicator produces a tactile signal which is felt by the wearer's foot." In one of the versions and in the claims, it is stated, "a piston and cylinder are used with the piston moving under the influence of a threshold of pressure exerted by the deformation of a compressible cavity member on which the user steps. The threshold pressure in the compressible cavity member is reached when a one-way force-activated release valve is activated." I insert this because I am also using air pressure in my device, however, there is no comparable nature to the patented device and my embodiment because I am utilizing a bladder, not a "piston and cylinder". Walczyk et al. did not disclose any kind of signal other than a "clicking sound" emanating from the device and, although skilled in the art, it was unobvious to the inventor to attach an LCD or gauge to an assistive walking device for a visual monitoring of the weight bearing.

U.S. Pat. No. 6,174,294 to Crabb et al (2001) teaches in the abstract "A lower limb load monitor for providing feedback to a patient or user when a preselected force load level is met or exceeded on a patient's or user's foot." Continuing, "The device includes one or more thin film force sensing elements positioned beneath the user's foot and connected with control means for providing a signal when a predetermined threshold force is met."

The inventor teaches a "control member connectable to a portion of the user's body at a location remote from said substrate." Then continues "an alarm signal generating member operatively connected with said signal processor to provide an alarm signal" and "indicating the preselected threshold level." In the SUMMARY OF THE INVENTION, it is again disclosed 'the control box is sufficiently compact so that it can be attached to the user's belt or hip area, the leg or other area surrounding the lower portion of the user's leg or foot.

Crabb et al, skilled in the art, did not consider having a gauge or LCD attached to an assistive walking device for visual observation of the weight bearing.

U.S. Pat. No. 7,878,990 to Al-Obaidi et al (2011) Claims "A gait training device for detecting and correcting improper weight distribution during movement of an individual's body," In the BACKGROUND OF THE INVENTION, the author relates the device to a patient "When physicians provide written orders to physical therapists regarding ambulatory training, they may prescribe 'partial weight bearing status". This device is described as having weight sensors "attached to the underside of each foot", a microcomputer and means for inputting pre-selected weights into the computer's memory." The information is analyzed in a computer and studied for appropriate target load. This patent and claims have no objective connection to my concept which is worn "out of the clinic" and to be worn and utilized in the activities of daily living of a user, at home, nursing home or other setting. The inventor, skilled in the art, had no consideration of a method to attach a gauge or LCD to an assistive walking device for user or caregiver to monitor.

U.S. Pat. No. 7,998,092 to Avni, et al (2011) claims in claim 1. "A force sensor system for use in monitoring weight bearing at a location on a person". In brief this system consists of "pockets inflated with air or liquid" and "a plurality of tubes, wherein at least one tube allows flow of air or liquid in and out of each of the pockets to a location remote from the pouch; and a plurality of pressure sensors" then further states, "each pressure sensor is disposed to detect the pressure applied to at least one pocket."

Further claims have the "pockets" arranged in a variety of locations on the human body, such as the insole, the heel, a knee and a palm. In claim 18, "A system as in claim 2, therein the feedback includes audio, visual and/or mechanical vibration feedback that prompts a patient to shift the balance of weight on the location and/or to adjust the patient's gait or standing posture.

This invention artfully describes a device suitable for rehabilitation of a patient suffering from a stroke. The claims do not identify where or how the "audio, visual or mechanical vibration" is connected to the body or to an assistive walking device. It is obvious that the device, using "pockets" which can be interpreted as "bladders" that I utilize in my device, while being workable, is very labor intensive for the user, caregiver and therapist to apply and monitor. The user or caregiver I envision may have physical and mental deficits that negate the ability to control or operate the device.

Therefore, I do not believe my device is relevant to this invention even though the authors are skilled in the art and it utilizes "pockets of air or liquid." It does not confine the urge to one surface of the device, as my device confines the urge to the upper surface of the bladder, and it does not specify a location for the visual adaptation I envision, attached to an assistive walking device for a user or caregiver to observe.

U.S. Patent 20080167580 to Avni, et al (2008) teaches in the abstract, "Apparatus (10) is provided for use with a shoe worn by the subject, the apparatus (10) including an insole system (20), adapted to be inserted into the shoe, the insole system (20) including a flexible insole (26) and at least one force sensor (28), adapted to generate a force measurement: and a control unit (24), adapted to receive the force measurement, and convert the force measurement to a weight measurement."

In brief, this device consists of a method for calibrating a flexible insole that is inserted into a shoe, the shoe is weighed multiple times to generate a set of force measurements and using a "look-up table containing force-to-weight conversion values applicable to the shoe." The primary problem with this device is the need to have specific sizes for specific shoe inserts with "at least one force sensor", a control unit and a monitoring system to alert the user of improper weight distribution. Again, the cost and time factors involved in preparation for use by the patient is extensive and expensive. My device is simple in design, easily applied to the user and easy for the user or caregiver to apply and monitor. The inventor, skilled in the art, has created a significant device, however, it does not meet or compete with the criteria I have envisioned in my device nor the claims I have authored.

U.S. Patent 20110130686 to Fenkell (2011) teaches, in brief, an electronic weight sensor for monitoring a load on a lower extremity or prosthetic device and a method of actuating an audible or visible alarm when the weight applied exceeds a predetermined weight. There is a control box, which includes the sounding or flashing of an alarm, described as "attached to the pants or other garment worn by the patient." Although, skilled in the art, Fenkell does not consider the importance of having a monitor, gauge or LCD attached to an assistive walking device. The inventor of this device also requires a source of electrical power described as a battery, which can fail, and the control box is not well placed visibly which does not fall within the scope of the present device described herein.

U.S. Patent 201102144501 to Ross, et al (2011) teaches, in brief, a device that comprises "a sensor body abutting the insole monitoring weight applied and transmitting the pressure data signal to a reporting device with the reporting device having a processor and a computer-readable medium for storing the pressure data." An alert mechanism such as a beeper, buzzer, flashing light, etc, therefore the processor can not only receive the readings from the pressure sensors, it can also alert the user when the predetermined thresholds have been exceeded. Again, this device requires an electrical power source and is designed more for being read and controlled by a person skilled in the profession and does not relate to the device I have created. The inventors, skilled in the art did not consider the ability to have a monitor, gauge or LCD attached to an assistive walking device and did not submit claims to that purpose.

ADVANTAGES

The devices patented to date generally employ an electronic signal sent to a sound-making or vibrating device that is worn at the ankle or waist of the user. A significant problem and risk with these devices is that the required amount of urge must be exceeded to cause the signal device to sound. This increases the danger of the user placing excess weight on the affected limb. At no time did Yaglou (805), Gradisar (999), Pfeiffer (375), Sipe (491), Goforth (918), Confer (930), Sugerman, et al (620), Knotts, et al (854), Thomas, et al (654), Gray (081), Schmidt, et al (351), Hajianpour (924), Walczyk (606), Crabb, et al (294), Al-Obaidi, et al (990), Avni, et al (092), Avni, et al (580), Fenkel (686) or Ross, et al (501) anticipate or claim using the devices taught by them to allow the user or a caregiver to visually monitor urge applied by the lower extremity, when restricted weight bearing is ordered for a patient, because it was unobvious to these individuals, skilled in the art, to place a gauge or Liquid Crystal Diode (LCD) in immediate sight by attaching the gauge or LCD to a walker or crutches.

Another problem with the devices researched is that they generally allow the user to fully extend the affected limb because the device is thin. This creates increased opportunity to apply significantly more weight bearing force, by direct urge applied through the skeletal hip, knee and ankle than desired. It is easier to maintain a prescribed limit of weight bearing when the user is required to flex the knee, even slightly, while advancing the body over the affected limb.

In regard to the above examples, devices in production are priced from $300.00 to $900.00. Therapists or facilities resist purchasing such devices. If a service provider acquires one of the above named devices they will utilize the one device on several patients causing a risk of contamination or cross infection. This is presently a severe problem in hospitals with an increase of infections, such as Hepatitis C. The device I am proposing may be manufactured and distributed at a much lower cost and issued personally for the user, reducing the opportunity for infection.

Many patients requiring limited weight bearing on one limb suffer from dementia, limited cognition or loss of short term memory and require caregiver assistance to monitor the prescribed limit on weight bearing. A significant risk with the majority of the existing devices as described above is the inability of a caregiver to properly monitor the weight being applied. If the caregiver must wait for the device to sound a warning, the appropriate weight-bearing limit has been exceeded and is hazardous to the user. The device claimed here provides a visual monitor indicating to the user and caregiver the amount of weight being applied. Failure of the device is immediately evident if the gauge does not move because of failure of the bladder to hold a prespecified commencement level of pressure in the bladder readable and observable on the gauge or LCD.

My device is specifically useful for visually monitoring the weight being applied to a foot during periods of walking. This can also monitor weight bearing during the process of moving or transferring from sit to stand, moving from bed to chair and similar activities of daily living requiring monitored lower extremity weight bearing. When a desired amount of weight is placed upon the foot portion of the device, a readable monitor with movement of the needle of an analog gauge or with Liquid-crystal Diode, (LCD) exhibiting numbers is observable by the user and any caregiver.

The device I describe is quite simply a modification of a standard blood pressure cuff, in particular, the device used in emergency rooms which employs a gauge approximately four inches square attached by a hose or tube to a bladder encased in a sleeve allowing it to be placed around the arm of a patient and using manual (or electronically) to inflate the cuff and record the blood pressure of the individual. Imagine the number of intelligent, highly educated and creative individuals and manufacturers, skilled in the art, who have looked at a sphygmomanometer and did not see what I see in the modification of this device. If they had, this would have been available years ago.

My concept is to change the bladder to a bladder encased in a shoe like appendage with a tube or hose connected to a gauge, the gauge then attached to an assistive walking device to visually monitor the amount of weight or urge applied by the wearer or a caregiver.

Accordingly, the advantages of the present device are to provide a visual aide in the form of a gauge or a LCD. The gauge or LCD being brightly colored and placed at a close proximity to a line of sight for the user and/or a caregiver by being attached to the horizontal front bar of a walker or to a bar attached to a crutch;

(a) to provide for the monitoring of a designated amount of weight placed on a foot during ambulatory activity;
    (b) to provide an observable device for a person who is required to limit their weight on one lower extremity;
    (c) to provide an observer or caregiver with an accurate assessment of the amount of weight being applied without regard to the educational level or proficiency of the observer;
    (d) to provide a safe device to reduce the risk of applying excessive weight to an extremity when a physician prescribes monitored weight bearing on one foot;
    (e) to provide an affordable device for monitoring weight bearing; and
    (f) to provide a measuring device for weight bearing that can be issued to a person required to limit weight bearing on one foot.

SUMMARY

In accordance with the present invention, one embodiment is a device made from "off the shelf" components of a gauge or LCD, attached to a walker or a crutch, with the gauge or LCD visible to the user or caregiver, the said gauge or LCD connected by a hose or tube to a bladder confined in a fabricated foot component attachable to a human foot by appropriately placed straps, the said bladder filled with air or liquid to a pressure consistent with a zero point on the said gauge or LCD then allowing the amount of urge applied by the user on the upper surface of said bladder to be observable on the gauge or LCD. The purpose of this device is to allow a user or observer to monitor the amount of weight placed on an injured or impaired lower extremity when such restriction of weight bearing has been ordered by a professional. The device is expendable to avoid infection or contamination by another user.

DRAWINGS

Figures

In the drawings.

DRAWINGS

Reference Numerals 1 foot appendage component containing bladder
2 tube or hose
3 gauge
4 assistive walking device, i.e. walker
5 user
6 user's lower extremity requiring limited weight bearing
7 horizontal bar holding gauge
8 pliable upper surface of bladder
9 rigid lower surface of foot appendage component
10 bladder nozzle encased in foot appendage component
11 indicator needle
12 readable surface of gauge
13 segmentation of gauge
14 needle/line for zero point of urge
15 nozzle
16 three way connector
17 squeeze bulb
18 valve
19 bracket
20 straps holding foot appendage component
21 assistive walking device, i.e. crutch
22 brackets holding horizontal bar
23 rigid sides of foot appendage component

DETAILED DESCRIPTION

Preferred Embodiment

Figure 1:
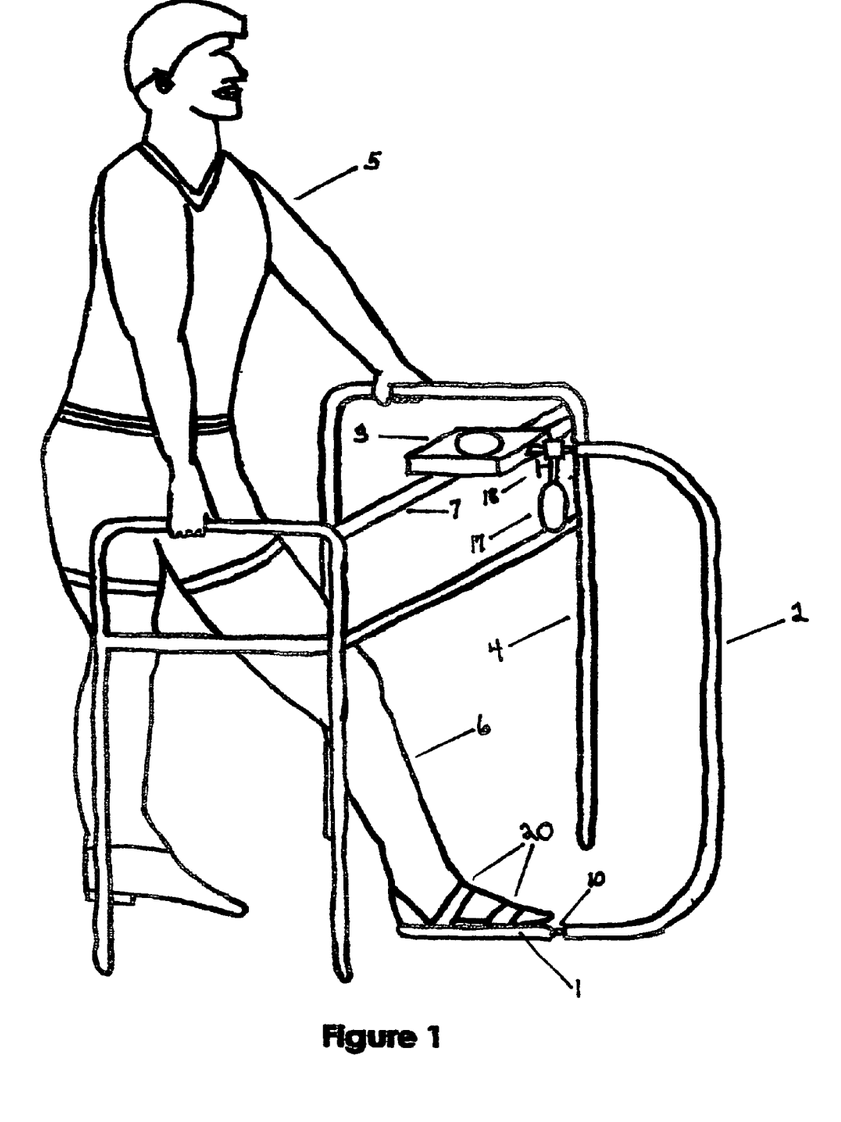
FIG. 1 is a perspective view of a first embodiment of my invention with a user grasping a standard walker with an observable, readable gauge on the center of the walker's cross bar. A hose extends downward from the gauge to a bladder encased in a foot appendage component.
Figure 2:
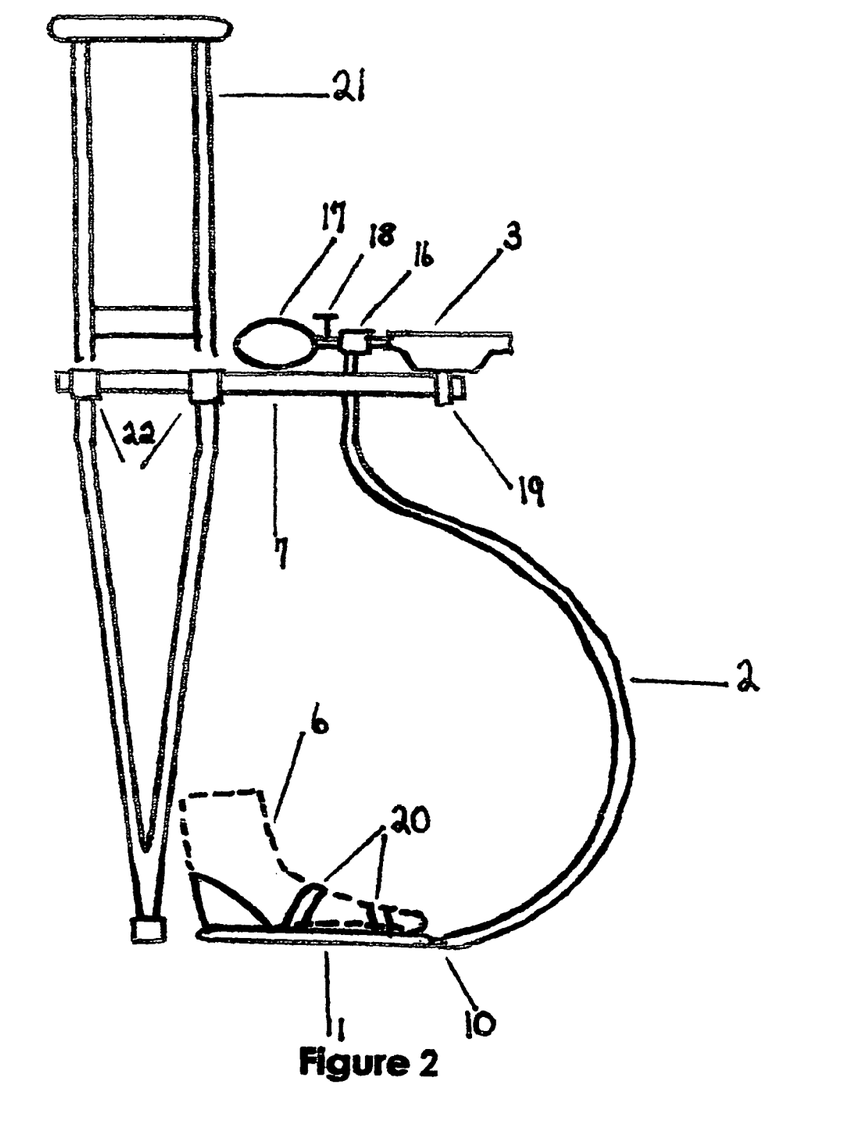
FIG. 2 shows a side view of a standard crutch with an added horizontal bar to which the gauge device is attached, with a hose from the gauge leading downward to the foot appendage component.
Figure 3:
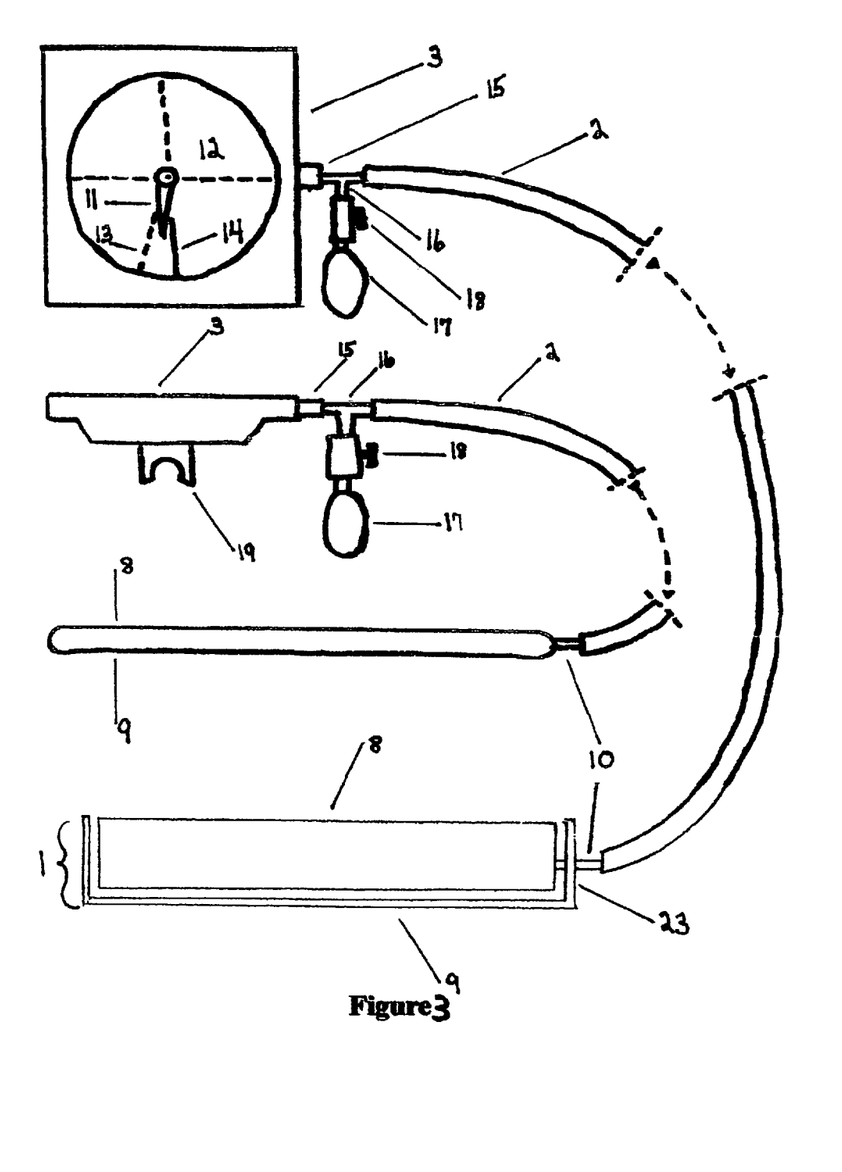
FIG. 3 is a visualization of the gauge attached by hose to a bladder encased in a rigid containment of the foot appendage component.

The first embodiment of the device is illustrated in FIG. 1 with further detailing in FIGS. 2 and 3. FIG. 1 represents user (5), standing with walker (4), wearing foot appendage component containing bladder (1). This is fastened by straps (20) to the foot of user's lower extremity requiring limited weight bearing (6). By stepping on said bladder (1) urge is transmitted via tube or hose (2) fastened to bladder (1) by nozzle (10) extending upward to three way connector (16) seen in FIG. 2. Opposing end of said connector (16) attaches to nozzle of said gauge (3). Said user (5) can visualize said gauge (3) attached to horizontal bar (7) of said walker (4) by bracket (19). Said user (5) or caregiver can easily observe urge applied by said foot (6) requiring limited weight bearing. Squeeze bulb (17) attached to said connector (16) forces air into bladder (1) to establish a zero point of pressure with indicator needle (14) noted in FIG. 3. Valve (18) seen in FIG. 2 locks pressure to hold said zero point of urge with starting line (14).

Said gauge (3) as described and used in the prototype is WelchAllyn®, Tycos® Model Number CE0050. Said squeeze bulb (17) is Tycos® Model 01. Said gauge (3) measures urge as millimeters of Mercury can be converted to pounds of pressure per cubic inch. Said gauge (3) said bulb (17) may be a different model or manufacturer. Several have same capabilities as the WelchAllyn® Models mentioned. Liquid-crystal Diode is not shown in drawings may replace said gauge (3). LCD is utilized by manufacturers such as Health O meter Model 349KLX Digital Floor Scale with 0.5 inch LCD display. This model can be remote by wireless from LCD to said bladder (1). The embodiment described above attaches to said bar (7) by said bracket (19). Observation by said user (5) or caregiver is apparent. Straps (20) may be Velcro® or buckles.

FIG. 2 is a representation of the device applied to a crutch with said horizontal bar (7) fastened by brackets (22) holding said gauge (3). Allowing said user (6) to visually monitor urge applied to said bladder (1).

FIG. 3 illustrates said gauge (3) showing readable surface (12) with indicator needle (11) attached at the center. Said needle (11) sweeps over said readable surface (12). Said surface (12) segmented into sections with lines (13). Specifically designated line is zero point of urge (14), for said needle (11). Number of sections vary and may be color coded. Said gauge (3) has appended nozzle (15) attached to said connector (16). Said hose (2) connected to second nozzle of said connector (16) leads downward to said bladder (1). Third nozzle of said connector (16) attaches to valve (18). Said valve (18) connects to said bulb (17). Said bracket (19) secures said gauge (3) to said walker (4) or said crutch (21) said gauge (3) is observable by said user (5) or caregiver. Said bulb (17) when compressed, forces air into said bladder (1). Pressure increases in said bladder (1) until said needle (11) on said gauge (3) is centered on said starting point (14) for measurement of urge applied to pliable upper surface of bladder (8), shown in FIG. 3. Said valve (17) allows air to be impelled or expelled from said bladder (1).

CONCLUSIONS, RAMIFICATIONS AND SCOPE

As an overview, a patient's physician prescribes weight bearing restrictions for a specific medical condition. Visual Warning Device for Weight Bearing in FIG. 1 is designed to assist said user (5), or caregiver, in monitoring visually, weight applied to lower extremity (6) when said user (5) has a condition that necessitates restricted weight bearing. Said gauge (3) noted in FIG. 1 is observable by said user (5) or caregiver standing near the user.

A variation of the preferred embodiment may have said bladder (1) pre-pressurized by the manufacturer with said needle (11) preset to said line (14). Said bladder (1) may contain air or fluid. This would eliminate the need for said bulb (17), said connector (16) and said valve (18) described in the preferred embodiment. Said gauge (3) would connect by said tube or hose (2) directly to said bladder (1).

Advantages

From the description above, the user can overcome all of the stated problems. Monitoring with the bathroom scale is a momentary limit requiring memorization of weight borne. Observation of gauge (3) is available with every step by said user (5) or a caregiver standing with the user (5). With the device described here, there are more reliable outcomes. Sounding of an alarm or vibration is not necessary.

The problem of the user having short term memory loss or dementia is resolved with caregiver visually monitoring weight bearing, before weight exceeds the limits prescribed by the medical professional. This allows increased physical activity. Prior to having such a device, the patient would have to wait for weight bearing to be increased by the physician before recovery or walking can start in a safe environment.

If a prescription is for none or touch weight bearing, the device described above accommodates this order. There is stability of balance skills when allowing a little weight on the affected foot. Mild weight bearing encourages healing.

From the description above, a number of advantages of my visual weight bearing device become evident:
(a) By utilizing off-the-shelf components, the cost of manufacture will be dramatically reduced in the final application and therefore saves considerable expense for hospitals, Medicare, health insurance providers and the user. The device is inexpensive to manufacture and may be issued to the user as an expendable item allowing continuity of care. Initially, a licensed therapist can issue the unit with the user or caregivers to monitor. For example, the patient may transfer from hospital to Rehabilitation facility or to Nursing Home or to personal home while still having weight bearing limitations.
(b) Another advantage of this invention is the user may be prevented from fully extending his or her leg due to the thickness of bladder (1). Fully extending the leg further endangers the ability to limit weight bearing because of the undesired consequence of full weight bearing through a straight hip and knee joint combination which may apply immediate excessive pressure.

This device achieves its intended purposes and advantages through a new useful but unobvious combination of components utilized for other purposes. This device can be manufactured by utilizing an "off the shelf" said gauge (3), such as the Welch Allyn® Tycos® 509-Series Model with readable face modified to portioned sections as described in FIG. 3. A substitute for said gauge (3) is a second type of readable monitor which may be an LCD readable monitor, such as the LCD remote display utilized in the Tanita® Model BWB-627 Digital Physicians Scales. The LCD would register urge emanating from said bladder (1) in numerals.

Said tube (2) may be the same as Neoprene Coiled Tubing utilized in Welch Allyn® Tycos® 509-Series Part Number 5089-39. Inflation bulb, such as the Welch Allyn® Tycos® Part Number 5086-01 may be utilized as said bulb (17) for manually inflating said bladder (1). Said valve (18), is available as the Welch Allyn® Tycos® Part Number 5087-01.

Although the description above contains much specificity, this should not be construed as limitations on the scope of the invention rather as an exemplification of providing illustrations of the preferred embodiments of this invention. For example, bladder (1) could take a differing shape or be sized for differing feet or be shaped for left or right feet. The device could be utilized hydraulically instead of pneumatically or the device may have electronic sensors in said bladder (1) or instead of said bladder (1). Said Gauge (3) and said bladder (1) may be wireless eliminating said hose (2). The significance remains the ability of a user or caregiver to visualize the amount of weight borne.

I claim:

1. A device for visually monitoring human weight bearing for a user using an assistive walking device, the device comprising:
    a pressurizable bladder;
    a coupling mechanism configured to couple the pressurizable bladder to a human foot;
    a squeezable bulb coupled to the bladder to selectively control a pressure associated with the bladder;
    a gauge coupled to the bladder such that the gauge is configured to detect a first pressure associated with the bladder, visually indicate the first pressure associated with the bladder such that the user is enabled to adjust a weight bearing associated with the human foot based on the visual indication of the first pressure, and detect a second pressure associated with the bladder and the adjustment of the weight bearing; and
    an element contained within the bladder.

2. A device in accordance with claim 1 further comprising a valve coupled to the bladder and to the gauge.

3. The device in accordance with claim 1, wherein the element comprises at least one of air, a predetermined gas, and a predetermined liquid.

4. The device in accordance with claim 1, wherein the gauge comprises a Liquid-crystal Diode.

5. A device for visually monitoring human weight bearing for a user using an assistive walking device, the device comprising:
    a bladder;
    a coupling mechanism configured to couple the bladder to a human foot;
    a squeezable bulb coupled to the bladder to selectively control a pressure associated with the bladder; and
    a gauge coupled to the bladder such that the gauge is configured to indicate the pressure associated with the bladder.

6. A device in accordance with claim 5, wherein the bladder contains at least one of air, a predetermined gas, and a predetermined liquid.

7. A device in accordance with claim 5 further comprising at least one of a hose and a tube coupled to the bladder and to the gauge.

8. A device in accordance with claim 5, wherein the gauge is oriented such that the gauge is readable by a user operating the device.

9. A device in accordance with claim 5 further comprising at least one crutch coupled to at least one of the gauge and the bladder.

10. A device in accordance with claim 5 further comprising a walker coupled to at least one of the gauge and the bladder.

11. A device in accordance with claim 5, wherein the device comprises a valve coupled to the bladder and to the gauge.

12. A method of manufacturing a device for visually monitoring human weight bearing for a user using an assistive walking device, the method comprising:
   coupling a bladder to a foot using a coupling mechanism;
   coupling a squeezable bulb to the bladder to enable the user to selectively control a pressure associated with the bladder; and
   coupling a gauge to the bladder, such that the gauge is configured to visually indicate the pressure associated with the bladder.

13. The method in accordance with claim 12 further comprising filling the bladder with at least one of air, a predetermined gas, and a predetermined liquid.

14. The method in accordance with claim 12 further comprising orienting the gauge such that the gauge is readable by the user operating the device.

15. The method in accordance with claim 12 further comprising coupling at least one crutch to at least one of the gauge and the bladder.

16. The method in accordance with claim 12 further comprising coupling a walker to at least one of the gauge and the bladder.

17. The method in accordance with claim 12 further comprising coupling a valve to the bladder and to the gauge.

* * * * *